US011208394B2

(12) United States Patent
Dauenhauer et al.

(10) Patent No.: US 11,208,394 B2
(45) Date of Patent: Dec. 28, 2021

(54) CHEMICAL PROCESS TO MANUFACTURE BRANCHED-CAPROLACTONE

(71) Applicant: Regents of the University of Minnesota, Minneapolis, MN (US)

(72) Inventors: Paul J. Dauenhauer, Shoreview, MN (US); Daniel J. Lundberg, Minneapolis, MN (US); David J. Lundberg, Minneapolis, MN (US); Marc A. Hillmyer, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 16/562,971

(22) Filed: Sep. 6, 2019

(65) Prior Publication Data
US 2020/0087276 A1 Mar. 19, 2020

Related U.S. Application Data

(60) Provisional application No. 62/732,196, filed on Sep. 17, 2018.

(51) Int. Cl.
*C07D 313/04* (2006.01)
(52) U.S. Cl.
CPC .................. *C07D 313/04* (2013.01)
(58) Field of Classification Search
CPC .................................................. C07D 313/04
(Continued)

(56) References Cited

U.S. PATENT DOCUMENTS 4,304,943 A * 12/1981 Bjornson ............. B01J 23/8892
568/361
4,313,879 A 2/1982 Klenk et al.
(Continued)

FOREIGN PATENT DOCUMENTS

DE 2704345 8/1978
GB 1408129 * 1/1975
(Continued)

OTHER PUBLICATIONS

Li, "Hydrogenation of o-cresol on platinum catalyst: Catalytic experiments and first-principles calculations." Applied Surface Science, 2017 393,212-220.*

(Continued)

*Primary Examiner* — Taylor V Oh
(74) *Attorney, Agent, or Firm* — Fish & Richardson P.C.

(57) ABSTRACT

Synthesizing an alkyl-caprolactone includes hydrogenating an alkyl-phenol to yield a first mixture comprising an alkyl-cyclohexanone and an alkyl-cyclohexanol; separating the alkyl-cyclohexanone from the first mixture to yield a first portion of a purified alkyl-cyclohexanone; oxidizing the first portion of the purified alkyl-cyclohexanone to yield a second mixture comprising an alkyl-caprolactone, the alkyl-cyclohexanone, and the alkyl-cyclohexanol; separating the alkyl-caprolactone from the second mixture to yield a third mixture comprising the alkyl-cyclohexanone and the alkyl-cyclohexanol; combining the third mixture and the first mixture in to yield a fourth mixture; separating the alkyl-cyclohexanone from the fourth mixture to yield a second portion of the purified alkyl-cyclohexanone; oxidizing the second portion of the purified alkyl-cyclohexanone to yield a fifth mixture comprising the alkyl-caprolactone, the alkyl-cyclohexanone, and the alkyl-cyclohexanol; separating the alkyl-caprolactone from the fifth mixture; and combining the (Continued)

alkyl-caprolactone from the fifth mixture with the alkyl-caprolactone from the second mixture.

30 Claims, 3 Drawing Sheets

(58) Field of Classification Search
USPC .................................................. 549/272
See application file for complete search history.

(56) References Cited

U.S. PATENT DOCUMENTS

| | | | |
|---|---|---|---|
| 4,353,832 A * | 10/1982 | Lecloux | C07D 315/00 549/272 |
| 5,981,769 A | 9/1999 | Baur et al. | |
| 6,156,910 A | 12/2000 | Ueno | |
| 6,531,615 B2 | 3/2003 | Rocca et al. | |
| 6,936,724 B2 | 8/2005 | Ohara et al. | |
| 8,217,186 B2 | 7/2012 | Pinkos et al. | |
| 8,247,580 B2 | 8/2012 | Pinkos et al. | |
| 8,802,897 B2 | 8/2014 | Neumann et al. | |
| 9,388,107 B2 * | 7/2016 | Martens | C07D 223/10 |
| 2004/0087804 A1 | 5/2004 | Ohara et al. | |
| 2013/0217898 A1 * | 8/2013 | Ishihara | C07D 323/04 549/272 |

FOREIGN PATENT DOCUMENTS

| | | |
|---|---|---|
| JP | H11140075 | 5/1999 |
| WO | WO2017155441 | 9/2017 |
| WO | WO2018063049 | 4/2018 |

OTHER PUBLICATIONS

Product and Process Design Principles, 4th ed., Seider et al. (eds.), 2017, Chapter 17, 498-546.

Roman-Leshkov et al., "Activation of carbonyl-containing molecules with solid lewis acids in aqueous media," ACS Catalysis, Sep. 2011, 1(11): 1566-1580.

Ryans et al., "Run Clean with Dry Vacuum Pumps," Chem. Eng. Progress, Oct. 2001, 97(10):32-41.

Satterfield, "Trickle-Bed Reactors" AlChE Journal, Mar. 1975, 21(2):209-228.

Schutyser et al., "Chemicals from lignin: an interplay of lignocellulose fractionation, depolymerisation, and upgrading," Chem. Soc. Reviews, Feb. 2018, 47(3):852-908.

Schutyser et al., "Selective Nickel-Catalyzed Conversion of Model and Lignin-Derived Phenolic Compounds to Cyclohexanone-Based Polymer Building Blocks," ChemSusChem, May 2015, 8(10):1805-1818.

Shafaghat et al., "Catalytic hydrogenation of phenol, cresol and guaiacol over physically mixed catalysts of Pd/C and zeolite solid acids," RSC Advances, Apr. 2015, 5(43):33990-33998.

Spanjers et al., "Branched diol monomers from sequential hydrogenation of renewable carboxylic acids," ChemCatChem, Jul. 2016, 8(19):3031-3035.

Sun et al., "Implementation of Ethanol Dehydration Using Dividing-Wall Heterogeneous Azeotropic Distillation Column," Separ. Sci. Technology, May 2011, 46(8):1365-1375.

Thaore et al., "Sustainable production of chemical intermediates for nylon manufacture: A techno-economic analysis for renewable production of caprolactone," Chem. Eng. Res. Design, Jul. 2018, 135:140-152.

TheMarketReports.com [online], "Global Caprolactone Market Research Report 2018," Dec. 2018, retrieved on Sep. 9, 2020, retrieved from URL<https://www.themarketreports.com/report/global-caprolactone-market-research-report-2018>, 6 pages.

Trambouze, "Countercurrent Two-Phase Flow Fixed Bed Catalytic Reactors," Chem. Eng. Science, 1990, 45 (8):2269-2275.

Trollsås et al., "Highly Branched Block Copolymers: Design, Synthesis, and Morphology," Macromolecules, Jul. 1999, 32(15):4917-4924.

Van de Vyver et al., "Emerging catalytic processes for the production of adipic acid.," Catal. Sci. Technology, Jun. 2013, 3(6):1465-1479.

Wang et al., "Organometallic and enzymatic catalysis for ring opening copolymerization of ε-caprolactone and 4-methyl-ε-caprolactone," J. Polym. Sci., Part A: Polym. Chemistry, Dec. 2011, 49(24):5293-5300.

Watts et al., "Strong, resilient, and sustainable aliphatic polyester thermoplastic elastomers," Biomacromolecules, May 2017, 18(6):1845-1854.

Williams et al., "Cycloaddition of Biomass-Derived Furans for Catalytic Production of p-Xylene," ACS Catalysis, Apr. 2012, 2(6):953-939.

Woodruff et al., "The return of a forgotten polymer—Polycaprolactone in the 21st century," Prog.Polym. Science, Oct. 2010, 35(10):1217-1256.

Xiao et al., "A highly stretchable bioelastomer prepared by UV curing of liquid-like poly(4-methyl-ε-caprolactone) precursors," J. Mater. Chemistry B, Jan. 2017, 5(3):595-603.

Xiao et al., "Synthesis of biodegradable chiral polyesters by asymmetric enzymatic polymerization and their formulation into microspheres," Soft Matter, Jan. 2008, 4(3):593-599.

Xu et al., "Selective Hydrogenation of Phenol to Cyclohexanone over Pd-HAP Catalyst in Aqueous Media," ChemCatChem, Aug. 2015, 7(16):2485-2492.

Xu et al., "Synthesis, Self-Assembly, and Drug Delivery Characteristics of Poly(methyl caprolactone-co-caprolactone)-b-poly(ethylene oxide) Copolymers with Variable Compositions of Hydrophobic Blocks: Combining Chemistry and Microfluidic Processing for Polymeric Nanomedicines," ACS Omega, Aug. 2017, 2(8):5289-5303.

Yakabi et al., "Continuous Production of Biorenewable, Polymer-Grade Lactone Monomers through Sn-β-Catalyzed Baeyer-Villiger Oxidation with H2O2," ChemSusChem, Sep. 2017, 10(18):3652-3659.

Yakabi et al., "Selectivity and Lifetime Effects in Zeolit-Catalysed Baeyer-Villiger Oxidation Investigated in Batch and Continuous Flow," ChemCatChem, Nov. 2016, 8(22):3490-3498.

Yang et al., "Aqueous-phase hydrodeoxygenation of highly oxygenated aromatics on platinum," Green Chemistry, Feb. 2014, 16(2):675-682.

Zhu et al., "Sustainable Polymers from Renewable Resources," Nature, Dec. 2016, 540:354-362.

Zupancich et al., "Aqueous dispersions of poly(ethylene oxide)-b-poly(γ-methyl-ε-caprolactone) Block Copolymers," Macromolecules, Jun. 2006, 39(13):4286-4288.

Abdelrahman et al., "Biomass-Derived Butadiene by Dehydra-Decyclization of Tetrahydrofuran," ACS Sustainable Chem. Engineering, Apr. 2017, 5(5):3732-3736.

Abdelrahman et al., "Renewable Isoprene by Sequential Hydrogenation of Itaconic Acid and Dehydra-Decyclization of 3-Methyl-Tetrahydrofuran," ACS Catalysis, Jan. 2017, 7(2):1428-1431.

Argyle et al., "Heterogeneous Catalyst Deactivation and Regeneration: A Review," Catalysts, Feb. 2015, 5(1) 145-269.

Averous et al., "Properties of thermoplastic blends: starch-polycaprolactone," Polymer, May 2000, 41(11):4157-4167.

Azimi et al., "Poly (ε-caprolactone) Fiber: An Overview," J. Eng. Fibers Fabrics, Sep. 2014, 9(3):74-90.

Bioplastics guide [online], "Bioplastics—Market and trends," available on or before Dec. 4, 2017, retrieved Sep. 9, 2020, retrieved from URL<http://www.bioplastics.guide/ref/bioplastics/market-and-trends/>, 7 pages.

Brink et al., "The Baeyer-Villiger Reaction: New Developments towards Greener Procedures," Chem. Reviews, Aug. 2004, 104(9):4105-4123.

Chemical Engineering Economics, reprint ed., Garrett (ed.), 2013, Appendix, 306.

Cho et al., "Renewable p-Xylene from 2,5-Dimethylfuran and Ethylene using Phosphorous-Containing Zeolite Catalysts," ChemCatChem, 2017, 9(3):398-402.

(56) References Cited

OTHER PUBLICATIONS

Corma et al., "Sn-zeolite beta as a heterogeneous chemoselective catalyst for Baeyer-Villiger oxidations," Nature, Jul. 2001, 412:423-425.
CRC Handbook of Chemistry and Physics, 88th ed., Lide (ed.), Oct. 2007, Section 6, 171-172.
Davis et al., "Process Design and Economics for the Conversion of Lignocellulosic Biomass to Hydrocarbons: Dilute-Acid and Enzymatic Deconstruction of Biomass to Sugars and Catalytic Conversion of Sugars to Hydrocarbons," National Renewable Energy Laboratory, Technical Report No. NRL/TP-5100-62498, Mar. 2015, 133 pages.
Davis et al., "On the mechanism of selective oxidation of 5-hydroxymethylfurfural to 2,5-furandicarboxylic acid over supported Pt and Au catalysts," Green Chemistry, Jan. 2012, 14(1):143-147.
De Hoe et al., "Sustainable Polyester Elastomers from Lactones: Synthesis, Properties, and Enzymatic Hydrolyzability," J. Am. Chem. Society, Jan. 2018, 140:963-973.
DeWilde et al., "Kinetics and Mechanism of Ethanol Dehydration on γ-Al2O3: The Critical Role of Dimer Inhibition," ACS Catalysis, Mar. 2013, 3(4):798-807.
Hillmyer, "The Promise of Plastics from Plants," Science, Nov. 2017, 358(6365):868-870.
Huang et al., "Conversion of furfural to 1,5-pentanediol: Process synthesis and analysis," ACS Sustainable Chem. Engineering, Apr. 2017, 5(6):4699-4706.
ICFAR.ca [online], "What is Lignin?", available on or before Feb. 20, 2016, via Internet Archive: Wayback Machine URL<https://web.archive.org/web/20160220023200/http://www.icfar.ca/lignoworks/content/what-lignin.html>, retrieved an Sep. 9, 2020, URL<http://www.icfar.ca/lignoworks/content/what-lignin.html>, 3 pages.
IRS.gov [online], "How to Depreciate Property," Feb. 28, 2018, retrieved on Jul. 8, 2018, retrieved from URL<https://www.irs.gov/pub/irs-pdf/p946.pdf>, 115 pages.
Ishihara et al., "Direct ester condensation from a 1:1 mixture of carboxylic acids and alcohols catalyzed by hafnium(IV) or zirconium(IV) salts," Tetrahedron, 2002, 58(41):8179-8188.
Ishihara et al., "Scandium Trifluoromethanesulfonate as an Extremely Active Lewis Acid Catalyst in Acylation of Alcohols with Acid Anhydrides and Mixed Anhydrides," J. Org. Chemistry, Jul. 1996, 61(14):4560-4567.
Jakobsson et al., "Modeling of a countercurrent hydrogenation process" Chem. Eng. Res. Design, Feb. 2004, 82 (2):203-207.
Johnson Matthey, "PGM Market Report," May 2018, 48 pages.
Karp et al., "Renewable Acrylonitrile Production," Science, Dec. 2017, 358(6368):1307-1310.
Labet et al., "Synthesis of polycaprolactone: a review," Chem. Soc. Reviews, Dec. 2009, 38(12):3484-3504.
Lee et al., "Succeed at Gas/Liquid Contacting" Chem. Eng. Progress, Jul. 1999, 95(7):23-49.
Lee et al., "Synthesis and characterization of amphiphilic block copolymers from poly(ethylene glycol)methyl ether and 4-methyl-ε-caprolactone," Polymer, Apr. 2007, 48(9):2605-2612.
Lee et al., "Synthesis and Characterization of Temperature-Sensitive Block Copolymers from Poly(N-isopropylacrylamide) and 4-Methyl-ε-caprolactone or 4-Phenyl-ε-caprolactone," J. Appl. Polym. Science, Nov. 2010, 118(3)1634-1642.
Liu et al., "Enhanced Selectivity of Phenol Hydrogenation in Low-Pressure CO2 over Supported Pd Catalysts," ACS Sustainable Chem. Engineering, Oct. 2017, 5(12):11628-11636.
Liu et al., "Selective phenol hydrogenation to cyclohexanone over a dual supported Pd-Lewis acid catalyst," Science, Nov. 2009, 326(5957):1250-1252.
Lu et al., "Techniques for fabrication and construction of three-dimensional scaffolds for tissue engineering," Int. J. Nanomedicine, Jan. 2013, 8:337-350.
Lung Chien et al., "Design and control of acetic acid dehydration system via heterogeneous azeotropic distillation," Chem. Eng. Science, Aug. 2004, 59(21):4547-4567.
Luo et al., "Synthesis and catalytic activity of Sn-MFI nanosheets for the Baeyer-Villiger oxidation of cyclic ketones," ACS Catalysis, Oct. 2012, 2(12):2695-2699.
Luyben, "Control of the Heterogeneous Azeotropic n-Butanol/Water Distillation System," Energy Fuels, Sep. 2008, 22(6)4249-4258.
MacArthur, "Beyond Plastic Waste," Science, Nov. 2017, 358(6365):843.
Makshina et al., "Review of old chemistry and new catalytic advances in the on-purpose synthesis of butadiene," Chem. Soc. Reviews, Oct. 2014, 43(22):7917-7953.
MaterialSampleShop.com [online], "Polycaprolactone (PCL)—A polymer with a very low melting point," available no later than Sep. 17, 2018, retrieved on Sep. 9, 2020, retrieved from URL<https://www.materialsampleshop.com/products/polycaprolactone>, 4 pages.
Miremadi et al., "Chemical innovation: An investment for the ages" McKinsey on Chemicals, May 2013, 9 pages.
Motagamwala et al., "Toward biomass-derived renewable plastics: production of 2,5-furandicarboxylic acid from fructose," Sci. Advances, Jan. 2018, 4(1):eaap9722, 8 pages.
Okuda et al., "Efficient conversion of lignin into single chemical species by solvothermal reaction in water-p-cresol solvent," J. Phys. Condensed Matter, Apr. 2004, 16(14):S1325-S1330.
Park et al., "Multifunctional Cascade Catalysis of Itaconic Acid Hydrodeoxygenation to 3-Methyl-Tetrahydrofuran," ACS Sustainable Chem. Engineering, Jul. 2018, 6(7):9394-9402.
Peeters et al., "Lipase-Catalyzed Ring-Opening Polymerizations of 4-Substituted ε-Caprolactones: Mechanistic Considerations," Macromolecules, 2005, 38(13)5587-5592.
Perez et al., "Highly selective palladium supported catalyst for hydrogenation of phenol in aqueous phase," Catalysis Communications, Jul. 2011, 12(12):1071-1074.
Malikmammadov et al., "PCL and PCL-based materials in biomedical applications," J. Biomater. Sci. Polym. Edition, Oct. 2017, 29(7-9):863-893.
Petersen et al., "Synthesis and characterization of reactive PEO-PMCL polymersomes," Polym. Chemistry, Oct. 2010, 1(8):1281-1290.
Product and Process Design Principles, 4th ed., Seider et al. (eds.), 2017, Chapter 16, 479-485.

\* cited by examiner

CHEMICAL PROCESS TO MANUFACTURE BRANCHED-CAPROLACTONE

CROSS-REFERENCE TO RELATED APPLICATION

This application claims the benefit of U.S. Application No. 62/732,196 entitled "CHEMICAL PROCESS TO MANUFACTURE BRANCHED-CAPROLACTONE" and filed on Sep. 17, 2018, which is incorporated by reference herein in its entirety.

STATEMENT OF GOVERNMENT INTEREST

This invention was made with government support under CHE-1413862 awarded by the National Science Foundation. The government has certain rights in this invention.

TECHNICAL FIELD

This invention relates to a chemical process to manufacture branched-caprolactone.

BACKGROUND

The transition to a sustainable plastics economy requires the discovery of new, high-performing polymers that can be economically manufactured. Across all polymer types and market sectors, the potential of plastics from plants includes the opportunity to sustainably obtain the feedstocks (i.e., monomers) that are assembled into polymeric structures with strategic end-of-life options including biodegradation or recycling. Implementation of these biomass-derived materials will depend on the economics and environmental impact in all three life-cycle phases: synthesis and manufacturing, application, and end-of-life processing. Efficient manufacturing processes are needed to attain these goals.

SUMMARY

In a first general aspect, synthesizing an alkyl-caprolactone includes hydrogenating an alkyl-phenol to yield a first mixture comprising an alkyl-cyclohexanone and an alkyl-cyclohexanol; separating the alkyl-cyclohexanone from the first mixture to yield a first portion of a purified alkyl-cyclohexanone; oxidizing the first portion of the purified alkyl-cyclohexanone to yield a second mixture comprising an alkyl-caprolactone, the alkyl-cyclohexanone, and the alkyl-cyclohexanol; separating the alkyl-caprolactone from the second mixture to yield a third mixture comprising the alkyl-cyclohexanone and the alkyl-cyclohexanol; combining the third mixture and the first mixture in to yield a fourth mixture; separating the alkyl-cyclohexanone from the fourth mixture to yield a second portion of the purified alkyl-cyclohexanone; oxidizing the second portion of the purified alkyl-cyclohexanone to yield a fifth mixture comprising the alkyl-caprolactone, the alkyl-cyclohexanone, and the alkyl-cyclohexanol; separating the alkyl-caprolactone from the fifth mixture; and combining the alkyl-caprolactone from the fifth mixture with the alkyl-caprolactone from the second mixture.

Implementations of the first general aspect may include one or more of the following features.

In some implementations, the alkyl-phenol includes one or more of:

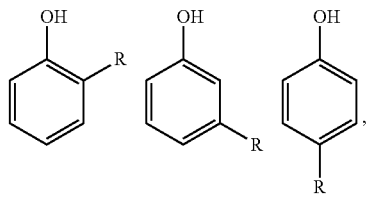

where the alkyl (R) is selected from the group consisting of methyl, ethyl, propyl, and iso-propyl. In one example, the alkyl-phenol is p-cresol. In certain examples, the alkyl-phenol includes a compound derived from lignin. In some implementations, hydrogenating the alkyl-phenol occurs in the absence of a solvent. In certain implementations, hydrogenating the alkyl-phenol occurs in the presence of a solvent. The solvent may be selected from the group consisting of undecane, dodecane, and tridecane. In one example, the solvent is dodecane.

In a second general aspect, synthesizing an alkyl-caprolactone includes hydrogenating an alkyl-phenol in a first reactor to yield a first stream comprising an alkyl-cyclohexanone; providing the first stream to a first distillation column to yield a second stream including the alkyl-cyclohexanone; providing the second stream to a second distillation column to yield a third stream including purified alkyl-cyclohexanone; oxidizing the purified alkyl-cyclohexanone in a second reactor to yield a fourth stream including an alkyl-caprolactone and the alkyl-cyclohexanone; providing the fourth stream to a third distillation column to yield a fifth stream including the alkyl-caprolactone and a sixth stream including the alkyl-cyclohexanone and water; removing some of the water from the sixth stream to yield a seventh stream; providing the seventh stream to a fourth distillation column to yield an eighth stream including the alkyl-cyclohexanone; and providing the eighth stream to the second distillation column.

Implementations of the second general aspect may include one or more of the following features.

In some implementations, the alkyl-phenol includes one or more of:

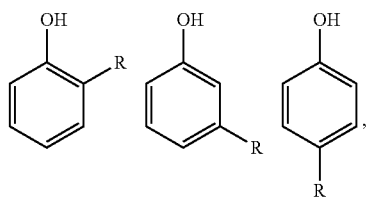

where the alkyl (R) is selected from the group consisting of methyl, ethyl, propyl, and iso-propyl. In one example, the alkyl-phenol is p-cresol. In certain examples, the alkyl-phenol includes a compound derived from lignin.

In some implementations, hydrogenating the alkyl-phenol occurs in the absence of a solvent. In certain implementations, hydrogenating the alkyl-phenol occurs in the presence of a solvent. The solvent may be selected from the group consisting of undecane, dodecane, and tridecane. In one example, the solvent is dodecane. The second stream may further include an alkyl-cyclohexanol.

Hydrogen may be removed from the first stream before the first stream is provided to the first distillation column. Removing the hydrogen from the first stream may include providing the first stream to a flash tank. The solvent may be removed from the first distillation column. Solvent removed from the first distillation column may be provided to the first reactor. The fourth stream may include an alkyl-hydroxy-hexanoic acid, an alkyl-adipic acid, or both. Unreacted alkyl-phenol may be removed from the first distillation column. The unreacted alkyl-phenol may be provided to the first reactor.

At least 80 wt % of the alkyl-phenol in the first reactor is typically converted to the alkyl-cyclohexanone. Less than 30 wt % of the purified alkyl-cyclohexanone is typically oxidized in the second reactor. Oxidizing the purified alkyl-cyclohexanone in the second reactor may include providing an oxidizing agent to the second reactor. Substantially all of the oxidizing agent in the second reactor may be reacted. In one example, the oxidizing agent includes hydrogen peroxide (e.g., an aqueous solution having at least 40 wt % hydrogen peroxide).

In some implementations, the third distillation column is operated under sub-atmospheric pressure. In certain implementations, the fifth stream is provided to a fifth distillation column. The fifth stream may include an alkyl-hydroxy-hexanoic acid, an alkyl-adipic acid, or both. In some cases, the fifth distillation column is operated below 5 atm or under sub-atmospheric pressure. In some implementations, the sixth stream undergoes heteroazeotropic distillation. At least one of the second stream, the fourth stream, the sixth stream, and the eight stream may include an alkyl-cyclohexanol.

The details of one or more embodiments of the subject matter of this disclosure are set forth in the accompanying drawings and the description. Other features, aspects, and advantages of the subject matter will become apparent from the description, the drawings, and the claims.

DETAILED DESCRIPTION

Emerging advanced polymers utilize branched cyclic lactones such as methyl-ε-caprolactone to produce biodegradable elastomers. Conventional poly(ε-caprolactone) (PCL) from straight-carbon-chain ε-caprolactone monomer produces a semi-crystalline material that can be effectively blended with other polymers such as starch or poly(ethylene oxide); the ester moieties in the polymer backbone also impart biodegradability. The branched variant, poly(methyl-ε-caprolactone) (PMCL), also benefits from biodegradability/hydrolyzability, but the addition of branching leads to an amorphous material with a low glass transition temperature ($T_g$=~60° C.). PMCL has also been utilized in the preparation of unique block co-polymers which self-assemble into polymersomes; combined polymer blocks also include poly(ethylene glycol)methyl ether, poly(n-isopropylacrylamide), poly(lactic acid), and poly(ethylene oxide).

Figure 1:
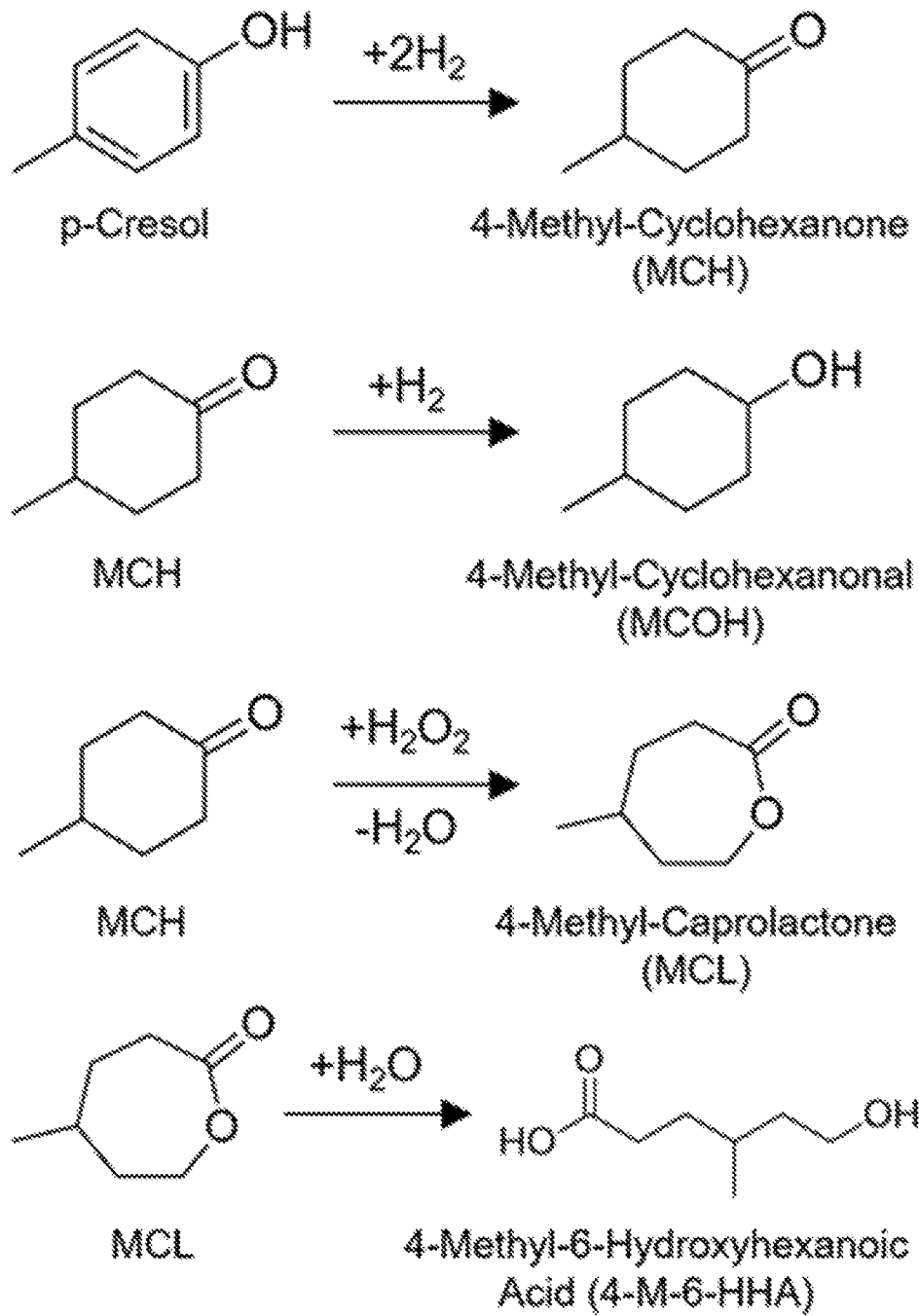
FIG. 1 depicts process chemistries for the conversion of p-cresol to 4-methyl-ε-caprolactone.

Resilient, strong, and degradable elastomers can be generated using alkyl-caprolactones, such as methyl-ε-caprolactone. The manufacture and application of these polymers relies on a viable chemical pathway between a sustainable biomass-derived feedstock and the alkyl-caprolactone produced at high purity. As depicted in FIG. 1, a chemical route known in the art utilizes alkyl-phenol. Suitable alkyl-phenols include

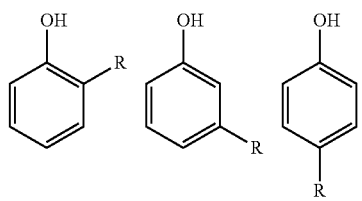

where the alkyl (R) is selected from the group consisting of methyl, ethyl, propyl, and iso-propyl. Examples of suitable alkyl-phenols include m-cresol, p-cresol, guaiacols, and compounds derived from lignins.

As part of a two-step process, alkyl-phenols are initially hydrogenated to form alkyl-cyclohexanones; for example, cresol is hydrogenated to form methyl-cyclohexanone. In the second reaction step, Baeyer-Villiger oxidation (BVO) of alkyl-cyclohexanones forms alkyl-caprolactones; for example, methyl cyclohexanone is oxidized to methyl-ε-caprolactone. These combined reaction steps provide flexibility to a range of lignin-derived alkyl-phenols while combining two selective chemistries capable of producing alkyl-caprolactones with a net high yield.

The hydrogenation of alkyl-phenols aims to selectively break aromaticity and form a cyclic ketone. Upon initial hydrogenation of the six-carbon ring, the hydroxyl group undergoes keto-enol tautomerization and forms a carbonyl; catalysts and conditions capable of selectively halting hydrogenation prior to carbonyl reduction with supported Pd, Pt, and Rh (e.g., palladium on hydroxyapatite, heterogeneous Pd with homogeneous Lewis acids such as $AlCl_3$).

The intermediate alkyl-cyclohexanone can be oxidized to alkyl-caprolactone via a BVO reaction with an oxidizing agent such as hydrogen peroxide in the presence of a heterogeneous Lewis acid catalyst, such as Sn-containing zeolites and other Sn-containing microporous and mesoporous materials, that can activate ketones in aqueous media. In some cases, higher conversion lowers the overall yield of alkyl-caprolactone product.

The major by-product of alkyl-cyclohexanone BVO is alkyl-hydroxyhexanoic acid. Referring to FIG. 1, the major by-product of methyl-cyclohexanone BVO is methyl-hydroxyhexanoic acid, which results from the hydrolysis of methyl-ε-caprolactone. Methyl-hydroxyhexanoic acid can be converted back to methyl-ε-caprolactone in a process that involves multiple fractionation and reaction steps.

By way of example, the combination of sequential alkyl-phenol reduction and oxidation via heterogeneous catalysis of cresol is described here as part of a chemical process with reaction, separation, and ancillary process equipment. Hydrogenation within a trickle-bed catalytic reactor converts cresol to methyl-cyclohexanone, which is then purified and sent to a liquid phase fixed-bed oxidation reactor. The resulting methyl-ε-caprolactone is then purified by distillation.

Figure 2:
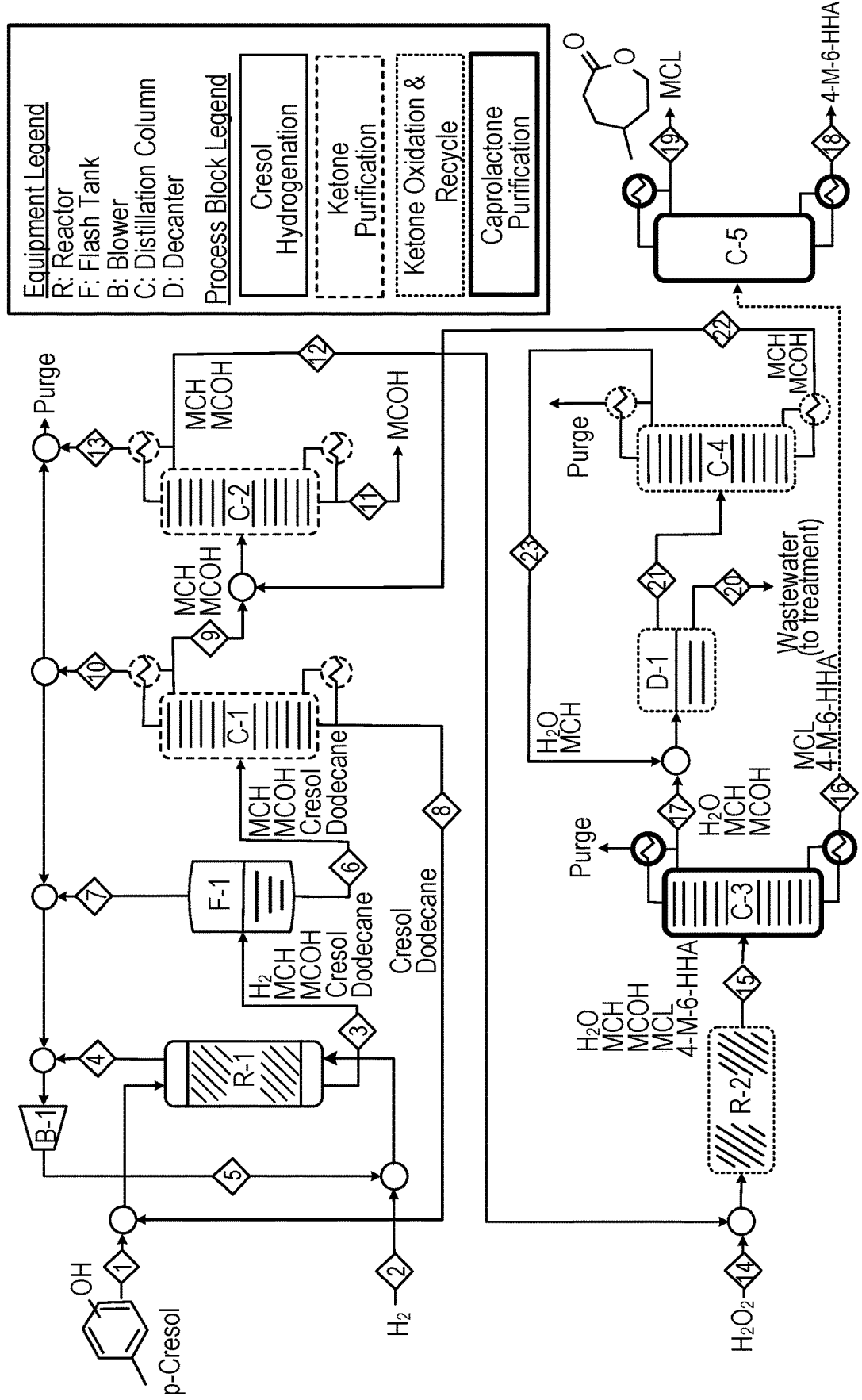
FIG. 2 depicts a process flow diagram for the conversion of p-cresol to 4-methyl-ε-caprolactone via hydrogenation (B-1, R-1, and F-1), ketone purification (C-1 and C-2), ketone oxidation (R-2, D-1, and C-4), and caprolactone purification (C-3 ad C-5).

Based on the chemistries of alkyl-phenol hydrogenation and BVO, the process depicted in FIG. 2 has been developed to assess the economic and technological feasibility of the conversion of p-cresol into 4-methyl-ε-caprolactone (MCL). The developed process combines the two subsequent reactions, recycle, and product purification steps for the hydrogenation of p-cresol to 4-methyl-cyclohexanone (MCH) and then the BVO of MCH to MCL. The process is divided into four blocks shown in FIG. 2: hydrogenation of p-cresol to MCH and vapor recovery, MCH purification, BVO of MCH to MCL with recycle of unreacted MCH, and the purification of MCL. Aspen Plus (V8.6 Aspen Technology) was employed to simulate the reaction, separation, and mass balances of the designed process. The Peng-Robinson equation of state was used to simulate all separation operations. The distillation columns were modeled using the Aspen RadFrac module.

In the designed process, liquid phase hydrogenation of p-cresol (stream 1) to MCH was performed under atmospheric pressure of hydrogen (stream 2) using a Pd/HAP catalyst. It was approximated that 98% conversion of p-cresol and 97% selectivity to MCH can be achieved at 75° C. Catalyst activity was directly taken to be 0.014 mol gcar$^{-1}$ hr$^{-1}$. n-Dodecane was used in the first reactor as a solvent to avoid the azeotrope formed from water and MCH. Two-phase fixed-bed trickle-bed reactor R-1 was modeled for liquid phase hydrogenation of p-cresol. It was assumed that deactivation of the Pd/HAP catalyst was mainly caused by formation of coke and not sintering due to the relatively low reaction temperature. Catalyst lifetime was approximated to be at least 15 hours; reactant feed was regularly switched between a parallel reactor, while the coke deposits in the empty reactor are removed by oxidation.

Initially, a mixture of p-cresol (stream 1) and n-dodecane (stream 8) with a reactant to solvent molar ratio of 0.187 (half the solubility limit of p-cresol in n-dodecane at 75° C., as estimated in Aspen Plus) was heated to reaction temperature (75° C.) and fed to the top of the reactor. Hydrogen (stream 2) was fed to the bottom of the reactor. Excess hydrogen was collected from the top of the reactor (stream 4) and recycled (stream 5) using blower B-1. Liquid effluent from the reactor (stream 3) was cooled to 45° C. and flashed at atmospheric pressure in flash tank F-1, where 8% of dissolved hydrogen was removed from the condensate. The flashed vapor was recycled through a recycle stream (stream 7) via the blower.

The liquid flash stream containing MCH, side product 4-methyl-cyclohexanol (MCOH), unreacted p-cresol, and n-dodecane solvent (stream 6) was pumped to distillation column C-1 where n-dodecane and p-cresol were recovered from the distillation column bottoms (stream 8) and recycled back to the hydrogenation reactor feed. The vapor distillate (stream 10) contained hydrogen and MCH that was recycled through the vapor recycle system. MCH and MCOH were recovered in the liquid distillate (stream 9), combined with recycled MCH and MCOH from C-4, and fed to second distillation column C-2 where MCOH was removed in the bottoms (stream 11) and pure MCH (99 mol %) was recovered in the liquid distillate (stream 12) and sent to BVO reactor R-2. The vapor distillate from C-2 (stream 13) was recycled through the vapor recycle system. A 5% fraction of recycled vapor from F-1, C-1, and C-2 was purged to reduce buildup of impurities in the process. Dehydrogenation of MCOH back to MCH was not considered in this process due to the high selectivity achieved in R-1.

MCH (stream 12) was mixed with a 50 wt % aqueous hydrogen peroxide solution (stream 14), heated to the reaction temperature of 50° C., and fed at 1.0 bar over a Sn-BEA catalyst in packed bed flow reactor R-2. Catalyst space time yield was based on batch experimental results of 24.5 g-lactone kgcat$^{-1}$ hr$^{-1}$ per cubic centimeter of reactor volume. In the reactor, the hydrogen peroxide reacted to completion with 20% of the fed MCH to generate 4-methyl-ε-caprolactone. 10% of the generated MCL was further hydrolyzed to produce 4-methyl-6-hydroxyhexanoic acid (4-M-6-HHA).

The liquid distillate from C-3 (stream 17) contained 80% of the MCH fed to R-2 and a significant amount of water from co-fed $H_2O_2$ aqueous solution as well as by-product water from the BVO reaction. Water is typically removed from the MCH before it is recycled to R-2 in order to prevent additional hydrolysis of MCL. This stream was cooled to 45° C. and sent to decanter D-1 where 90.7% of the water was removed in an aqueous stream. The aqueous phase from D-1 was sent to wastewater treatment (stream 20) and the organic phase (stream 21) was sent to distillation column C-4, the distillate of which contained a mixture of MCH and water that was recycled back to the decanter (stream 23). MCH with an impurity of MCOH was obtained from the bottom of C-4 (stream 22) and needed to be pumped back earlier in the process to C-2, where remaining MCH was purified to prevent accumulation of MCOH in the process.

By the method of recycle outlined in FIG. 2, 100% net conversion of MCH achieves 90% selectivity to MCL in the BVO reactor. The effluent from R-2 (stream 15) was sent to vacuum distillation column C-3 operated at 0.2 bar from which 4-M-6-HHA and MCL were recovered in the bottoms (stream 16) and sent to second vacuum distillation column C-5 operating at 0.056 bar. Pure, polymerization grade MCL (99.9 mol %) was recovered in the distillate from this column (stream 19), while the major by-product of 4-M-6-HHA was removed in the bottoms (stream 18). Vacuum distillation was used to ensure minimal MCL losses due to polymerization by reducing operating temperatures within C-3 and C-5. The column pressures were chosen to minimize polymerization.

The designed chemical process of FIG. 2 was developed to minimize the total project cost over the lifetime of 30 years. This base case design provided an initial technically feasible design which could be used to manufacture methyl-ε-caprolactone to the purity specifications of 99.9%. The combination of hydrogenation and BVO of p-cresol feedstock required four significant technical design decisions impactful to the overall base case process design.

The selection of a solvent for the two reactors (hydrogenation in R-1 and Baeyer-Villiger oxidation in R-2) directly affects catalyst performance while also impacting the cost of separations. In reactor R-2, purified methyl-cyclohexanone is combined with an aqueous stream of hydrogen peroxide; prior to C-2, the selected solvent will impact the catalytic performance of reactor R-1, flash tank F-1, and distillation column C-1.

The base case design selected n-dodecane as a solvent for hydrogenation based on its inertness during reaction and separability from the reactants and products. Alternative linear alkanes may be applicable in this process, but the hydrogenation solvent is desired to have a sufficiently low vapor pressure to remain in the liquid stream of flash tank F-1 while also being sufficiently heavy to flow out of the distillation column C-1 in stream 8 to recycle back to reactor R-1. Ultimately, n-dodecane was found to be the optimal linear alkane solvent due to its boiling point similar to that of p-cresol. If the hydrogenation reaction could maintain its selectivity and conversion while being operated without solvent, the size and operating cost of C-1 would decrease significantly. Additionally, the cost associated with C-1 could be lowered by implementing an alternative hydrogenation solvent or by running the reaction neat.

To recover and recycle the unreacted MCH from reactor R-2, heteroazeotropic distillation was required. The distillate of C-3, containing water, MCH, and trace amounts of MCOH was predicted by Aspen to form a heteroazeotrope, which is an azeotrope where the vapor phase coexists with two immiscible liquid phases. Traditionally, binary heteroazeotropes are separated as a two-distillation-column process wherein one column is fed the mixture to be separated, and the distillate of both columns is condensed, decanted, and each component-rich phase is refluxed back to a different column. Each of the two components is obtained as the bottoms of the respective column in which its phase is refluxed. It is important to note that heteroazeotropes are typically minimum boiling mixtures, thus explaining the counterintuitive result of obtaining pure streams of each component as bottom streams out of the columns.

A modified version of heteroazeotrope distillation was modeled in this process to recover MCH. Only a single column was required to obtain separation streams of water and the MCH/MCOH mixture. Aspen predicts the phase behavior of the water, MCH, and MCOH stream to form an extremely pure aqueous phase (>99.999 mol % water) and an organic phase containing 93.4 mol % MCH, 1.1 mol % MCOH, and 5.4 mol % water. This organic phase was sent to column C-4, where the distillate was collected and returned to be phase split in the decanter; the bottoms stream, comprising 98.7 mol % MCH and 1.2 mol % MCOH, was recycled back to the feed of column C-2.

In some cases, stream 22 is recycled back to reactor R-2, for example, with the addition of a distillation column to remove MCOH by-product. As depicted in FIG. 2, another approach is to recycle stream 22 to distillation column C-2, where MCOH could be separated within existing process equipment. MCH was then purified and sent to reactor R-2 to complete the recycle stream.

As mentioned in the introduction, the reconversion of the by-product 4-M-6-HHA back to MCL was not included in the designed process depicted in FIG. 2. Processes proposed for the industrial reconversion of 6-hydroxyhexanoic acid to ε-caprolactone typically require multiple reaction and separation steps, primarily the esterification and subsequent cyclization of the hydroxyacid, as well as long residence times which limit the recovered yield of ε-caprolactone to below 80%. Lab-scale synthetic routes towards this reconversion (primarily through Lewis acid catalysis) also typically require long reaction times and would generally necessitate multiple separation steps. Given the base case performance of the hydrogenation reaction, full recovery of the MCL from the 4-M-6-HHA by-product could only increase the total molar yield of the product to 95.1%, less than a 1% difference to the upper bound of MCL molar yield.

In the proposed process at 10 kton yr-1 p-cresol processed as depicted in FIG. 2, the maximum molar yield of MCL was 87.3% (the product of 97% selectivity and 90% total molar conversion of MCH in reactor R-2). The base case design had an overall molar yield of MCL of 85.6% based on catalytic performance of both reactors R-1 and R-2. Increasing the single-pass conversion of reactor R-2 results in a lower recycle flow rate to achieve an equivalent total molar conversion and leads to lower molar flow rates through all of the following process blocks—including columns C-2, C-3, and C-5.

The implementation of the two-stage hydrogenation/oxidation process with p-cresol is one potential process iteration, but there exists a broader range of potential alkyl-phenol mixtures that can serve as feedstock to manufacture alkyl-caprolactone monomers. Isomers of p-cresol (o,m-cresol, or mixtures of these components) will undergo similar processing, with only minor differences in separation and catalysis. The structure and size of the alkyl group on branched caprolactone monomer allows for alternative poly (alkyl-caprolactone) materials with properties tunable by the size and structure of the alkyl group. Additionally, the higher oxygen content in lignin-derived monomers introduces additional requirements for hydrogenation in the initial reactor, R-1. Despite these challenges, extending the proposed process of FIG. 2 to additional alkyl-phenols from lignin could provide a biorenewable pathway to alkyl-caprolactone monomers with economic potential.

The chemical manufacturing of methyl-ε-caprolactone was evaluated for technical process design and economic analysis by the combination of hydrogenation of p-cresol to methyl-cyclohexanone followed by Baeyer-Villiger oxidation. A two-stage process was proposed based on the two chemistries with accompanying separation to produce methyl-ε-caprolactone at 99.9% purity. The overall yield of the optimized base-case process was 85.7%, and sensitivity analysis of the major process variables identified improvements in overall selectivity via catalytic performance of the Baeyer-Villiger oxidation catalyst as an opportunity for improving the overall economics of the process.

Table 1 provides stream information for the process flow diagram of FIG. 2.

TABLE 1

Stream data for labeled streams (from process flow diagram in FIG. 2).

|  | 1 | 2 | 3 | 4 | 5 | 6 | 7 | 8 |
|---|---|---|---|---|---|---|---|---|
| Molar Flow p-Cresol | 11.600 | 0.000 | 0.357 | 0.000 | 0.001 | 0.357 | 0.000 | 0.315 |
| n-Dodecane | 0.021 | 0.000 | 62.176 | 0.000 | 0.012 | 62.163 | 0.012 | 62.143 |
| MCOH | 0.000 | 0.000 | 0.233 | 0.000 | 0.001 | 0.232 | 0.000 | 0.000 |
| MCH | 0.000 | 0.000 | 11.438 | 0.000 | 0.107 | 11.396 | 0.042 | 0.006 |
| MCL | 0.000 | 0.000 | 0.000 | 0.000 | 0.000 | 0.000 | 0.000 | 0.000 |
| 4-M-6-HHA | 0.000 | 0.000 | 0.000 | 0.000 | 0.000 | 0.000 | 0.000 | 0.000 |
| $H_2$ | 0.000 | 24.950 | 0.056 | 224.548 | 224.600 | 0.052 | 0.004 | 0.000 |
| $H_2O$ | 0.000 | 0.000 | 0.000 | 0.000 | 0.000 | 0.000 | 0.000 | 0.000 |
| $H_2O_2$ | 0.000 | 0.000 | 0.000 | 0.000 | 0.000 | 0.000 | 0.000 | 0.000 |
| Temperature (° C.) | 25 | 25 | 75 | 75 | 75 | 45 | 45 | 214 |
| Pressure (bar) | 1 | 1 | 1 | 1 | 1 | 1 | 1 | 1 |

TABLE 1-continued

Stream data for labeled streams (from process flow diagram in FIG. 2).

| | 9 | 10 | 11 | 12 | 13 | 14 | 15 | 16 |
|---|---|---|---|---|---|---|---|---|
| Molar Flow p-Cresol | 0.042 | 0.000 | 0.042 | 0.000 | 0.000 | 0.000 | 0.000 | 0.000 |
| n-Dodecane | 0.021 | 0.000 | 0.021 | 0.000 | 0.000 | 0.000 | 0.000 | 0.000 |
| MCOH | 0.231 | 0.001 | 0.230 | 0.549 | 0.000 | 0.000 | 0.549 | 0.001 |
| MCH | 11.322 | 0.067 | 0.222 | 55.394 | 0.001 | 0.000 | 44.284 | 0.008 |
| MCL | 0.000 | 0.000 | 0.044 | 0.000 | 0.000 | 0.000 | 9.999 | 9.954 |
| 4-M-6-HHA | 0.000 | 0.000 | 0.000 | 0.000 | 0.000 | 0.000 | 1.111 | 1.080 |
| $H_2$ | 0.002 | 0.050 | 0.000 | 0.002 | 0.000 | 0.000 | 0.002 | 0.000 |
| $H_2O$ | 0.000 | 0.000 | 0.000 | 0.007 | 0.000 | 20.916 | 32.026 | 0.000 |
| $H_2O_2$ | 0.000 | 0.000 | 0.000 | 0.001 | 0.000 | 11.078 | 0.000 | 0.000 |
| Temperature (° C.) | 140 | 140 | 170 | 157 | 157 | 25 | 50 | 181 |
| Pressure (bar) | 1 | 1 | 1 | 1 | 1 | 1 | 1 | 0.2 |

| | 17 | 18 | 19 | 20 | 21 | 22 | 23 |
|---|---|---|---|---|---|---|---|
| Molar Flow p-Cresol | 0.000 | 0.000 | 0.000 | 0.000 | 0.000 | 0.000 | 0.000 |
| n-Dodecane | 0.000 | 0.000 | 0.000 | 0.000 | 0.000 | 0.000 | 0.000 |
| MCOH | 0.548 | 0.000 | 0.001 | 0.000 | 0.608 | 0.548 | 0.060 |
| MCH | 44.294 | 0.000 | 0.008 | 0.000 | 52.397 | 44.294 | 8.103 |
| MCL | 0.044 | 0.010 | 9.945 | 0.000 | 0.045 | 0.044 | 0.000 |
| 4-M-6-HHA | 0.000 | 1.079 | 0.001 | 0.000 | 0.000 | 0.000 | 0.000 |
| $H_2$ | 0.000 | 0.000 | 0.000 | 0.000 | 0.000 | 0.000 | 0.000 |
| $H_2O$ | 29.649 | 0.000 | 0.000 | 29.642 | 3.035 | 0.007 | 3.028 |
| $H_2O_2$ | 0.000 | 0.000 | 0.000 | 0.000 | 0.000 | 0.000 | 0.000 |
| Temperature (° C.) | 30 | 202 | 145 | 40 | 40 | 160 | 81 |
| Pressure (bar) | 0.2 | 0.056 | 0.056 | 1 | 1 | 1 | 1 |

Hydrogenation Reactor Sizing.

Operating the hydrogenation reactor at atmospheric pressure allows significant cost savings associated with recycle and compression costs of effluent hydrogen gas from the reactor but amplifies mass transfer limitations. To mitigate mass transfer limitations, a countercurrent trickle-bed reactor was modeled for the hydrogenation of MCH. Countercurrent operation of a two-phase fixed bed trickle bed reactor provides increased mass transfer driving force for the dissolution of hydrogen leading to higher levels of conversion. The volume fraction of the reactor occupied by catalyst particles in trickle bed reactors varies based on configuration and packing. Neglecting the volume of vapor in the reactor, it was approximated that the catalyst and reaction solvent should occupy equal volumes, which would be appropriate for a single-phase fixed bed reactor or packed bubble column. Using the reported Pd-HAP catalyst performance of 0.0142 mol. Cresol hydrogenated per hr/gcat, and the assumption that residence time is equal to space time, a residence time of 660 seconds was chosen for the reactor. The amount of catalyst required for this reactor was calculated as follows, $$\text{Catalyst Required (g)} = \frac{\text{Molar Flow Rate of } p\text{-Cresol}\left(\frac{\text{mol}}{\text{s}}\right)}{\text{Residence Time } (hr) * 0.0142 \text{ mol} \cdot \text{Cresol hydrogenated} \cdot hr^{-1} \cdot gcat^{-1}} =$$

$$\frac{11.6 \frac{\text{kmol } p\text{-Cresol}}{hr} * \left(\frac{1000 \text{ kmol}}{\text{mol}}\right) * \left(\frac{1}{3600} s/hr\right)}{\left(\frac{660}{3600} hr\right) * 0.0142 \text{ mol} \cdot \text{Cresol hydrogenated} \cdot hr^{-1} \cdot gcat^{-1}} =$$

$$\boxed{4{,}460{,}000 \text{ g catalyst}}$$

This amount of catalyst occupies a volume of 3030 L (based on a density for the Pd-HAP catalyst of 3.1 g·cm$^{-3}$). The fraction of reactor volume occupied by catalyst is then calculated, knowing the volumetric flow rate of feed, $$\text{Reactor Volume Occupied by Catalyst (\%)} =$$

$$\frac{\text{Volume of Catalyst}}{\text{Volume of Catalyst} + \text{Residence Time} * \text{Feed Volumetric Flow Rate}} * 100 =$$

$$\frac{3030 \text{ L}}{3030 \text{ L} + (660 \text{ s}) * \left(4.6\frac{L}{s}\right)} * 100 = \boxed{50\%}$$

This value validates the original reactant/catalyst occupied volume assumption.

The rate of hydrogen feed to the reactor must be significantly greater than the consumption rate to ensure adequate mass transfer into the solvent. Practically, the aspect ratio of the reactor can be varied to prevent flooding and modify conversion at a specific vapor flow rate. To conservatively estimate the effects that excess hydrogen feed to the column will have on the process, the liquid effluent from the reactor was modeled to contain the solubility limit of hydrogen (as estimated in Aspen) at the reaction temperature, and a feed rate ten times the total rate of consumption of hydrogen was used to calculate the capital and operating cost of the vapor recycle blower.

BVO Reactor Sizing.

A packed bed plug flow reactor was modeled for the BVO of methyl-cyclohexanone to methyl-ε-caprolactone. The utilized catalyst performance was taken as 90% selectivity, 20% conversion. Additionally, flow experiments were performed with contact times of 9.75 minutes, although these experiments were not conducted at as high a selectivity as their batch experiments, their reported contact time is assumed to be suitable to achieve the reported batch performance in flow. It is noted that improvements in space-time-yield in flow compared to batch experiments were observed.

During reactor operation, 6,213,665 g/hr of methyl-cyclohexanone flows into the reactor, and overall 1,242,731 grams are converted per hour. The volumetric flow rate into the reactor is 127.7 L/min. Approximating that space-time is equal to residence time, the liquid volume is the reactor is calculated to be 1245.075 L for a 9.75 minutes residence time. Assuming that catalyst and packing occupy an equal amount of volume as reactant in the reactor total reactor volume is 2490.15 L or $2.49015 \cdot 10^6$ cm$^3$.

The mass of catalyst required for the reactor was then calculated as follows, $$\left(\frac{1,242,731 \text{ g Ketone Converted}}{1 \text{ hour}}\right) * \left(\frac{1}{2.49015 * 10^6 \text{ cm}^3 \text{ Reactor Volume}}\right) *$$

$$\left(\frac{\text{cm}^3 \text{ Reactor Volume} \cdot 1 \text{ Hour} \cdot \text{kg Catalyst}}{21.5 \text{ g Ketone Converted}}\right) = 0.0204 \text{ Kg Catalyst}$$

Vacuum Equipment Sizing.

The volumetric flow at suction conditions for the vacuum pumps (taken to be the condenser temperature and pressure) was calculated as the sum of vapor distillate and an estimate of air leakage. The following equation was used to estimate air leakage rate (W, lb/hr) based on system pressure (P, torr) and volume (V, ft$^3$), $$W=5+\{0.0298+0.03088*\ln(P)-0.0005733*[\ln(P)^2]\}*V^{0.66}$$

Column and vacuum specifications used for sizing the vacuum systems for columns 3 and 5 are listed in Table 2 below.

TABLE 2

Vacuum Column Specifications Used for Sizing Vacuum System.

| Column # | Column Volume (ft$^3$) | Column Operating Pressure (Torr) | Condenser Temperature (° C.) | Vapor Distillate Mass Flow Rate (lb/hr) |
|---|---|---|---|---|
| 3 | 78,000 | 150 | 30 | 27 |
| 5 | 26,400 | 50 | 145.4 | 0 |

The air leakage rate for column 3 was calculated as follows, $$W=5+\{0.0298+0.03088*\ln(150)-0.0005733*[\ln(150)^2]\}*78,000^{0.66}= \boxed{293 \text{ lb/hr}}$$

Approximating that the density of air and the vapor distillate is identical, the volumetric flow can be calculated using a density of 0.014334 lb/ft$^3$ for air at 30° C., 150 torr, and an estimated 10% humidity, $$\text{Volumetric Flow Rate}\left(\frac{\text{ft}^3}{\text{min}}\right) = \frac{\left(320\frac{\text{lb}}{\text{hr}}\right)}{0.014334\frac{\text{lb}}{\text{ft}^3}} = 22,300 \text{ ft}^3/hr$$

An overdesign factor of 1.5 was used, which gives a volumetric flow rate of 33,450 ft$^3$/hr and a corresponding mass flow rate of 480 lb/hr. Based on the calculated volumetric flow rate and given operating pressure, a single stage Steam jet ejector is appropriate for column three's vacuum system. The size factor (S) for a steam-jet ejector is in units of lb/hr·torr, $$S = \frac{480\frac{\text{lb}}{\text{hr}}}{150 \text{ torr}} = 3.2 \frac{\text{lb}}{\text{hr} \cdot \text{torr}}$$

Figure 3:
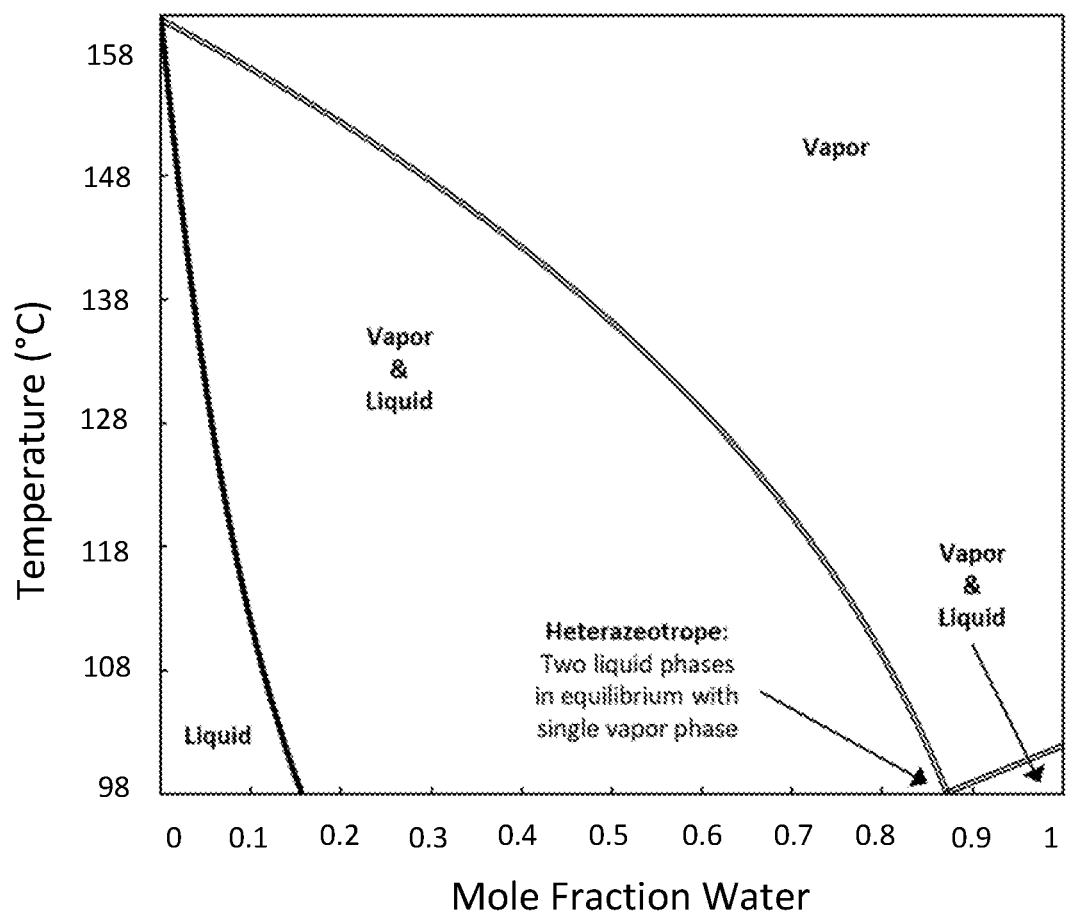
FIG. 3 shows a heteroazeotrope phase diagram of water and 4-methyl-cyclohexanone.

FIG. 3 shows a water/MCH heteroazeotrope phase diagram. At vapor-liquid mixtures that exceed 0.87 mole fraction water, the liquid phase is estimated to be pure water.

Solvent Optimization.

Column 1, which removes hydrogenation solvent and unreacted p-cresol from MCH and MCOH, accounts for more than half of the capital and operating costs of the "Ketone Purification" block, which is the largest process block contributor to MSP. The possibility of economic improvements by changing the hydrogenation solvent to higher or lower n-alkanes was explored. The process was simulated using various n-alkane solvents in the hydrogenation reactor for identical column 1 molar recovery and purity of MCH and MCOH in the distillate. The amount of solvent used was chosen to maintain p-cresol at half its solubility limit at 75° C. Economic and process details for these simulations in shown in Table 3 below.

TABLE 3

Costs and reflux ratio for column 1 associated with solvent selection.

| Solvent | Utility Costs ($/hr) | Installed Cost ($) | Reflux Ratio |
|---|---|---|---|
| N-Undecane | 120.37 | 8,187,200 | 8.65 |
| N-Dodecane | 68.16 | 7,524,200 | 1.52 |
| N-Tridecane | 82.35 | 8,100,200 | 0.92 |

Reflux ratio was found to decrease as alkane chain length increased, due to the greater difference in relative volatility from MCH and MCOH. However, the increased heat of vaporization and subsequent reboiler heat duty and utility costs of a longer chain alkane solvent lead to worse economic performance. Table 4 shows boiling point of linear alkane solvents and selected process species as estimated by Aspen Plus V8.6.

TABLE 4

Boiling Point of Linear Alkane Solvents and Selected Process Species as Estimated by Aspen Plus V8.6.

| Species | Boiling Point (° C.) |
|---|---|
| Pentane | 36.07 |
| Hexane | 68.73 |
| Heptane | 98.43 |
| Octane | 125.68 |
| Nonane | 150.82 |
| MCH | 170.00 |
| Decane | 174.155 |
| Undecane | 195.928 |
| p-Cresol | 201.98 |
| Dodecane | 216.323 |
| Tridecane | 235.466 |

A solvent with a boiling point lower than MCH but higher than the hydrogenation reaction temperature could be used, however this would necessitate an additional distillation column in the "Ketone Purification" block. Additionally, a reaction temperatures above 75° C. may lead to improved hydrogenation kinetics, which may further limit the minimum boiling point of the solvent.

Vacuum Distillation.

The operating pressures for C-3 and C-5 were chosen based on operating pressures for the analogous vacuum distillation purification of ε-caprolactone from a mixture of assorted low boiling components, 6-HHA, and adipic acid. Typically a fraction of low boilers is removed in the first column (C-3) and 6-HHA/adipic acid are removed in the second column (C-5). It was approximated that no loss of MCL through polymerization occurred in the base case process due to low distillation pressures and reflux ratios of these columns.

Although this disclosure contains many specific embodiment details, these should not be construed as limitations on the scope of the subject matter or on the scope of what may be claimed, but rather as descriptions of features that may be specific to particular embodiments. Certain features that are described in this disclosure in the context of separate embodiments can also be implemented, in combination, in a single embodiment. Conversely, various features that are described in the context of a single embodiment can also be implemented in multiple embodiments, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular embodiments of the subject matter have been described. Other embodiments, alterations, and permutations of the described embodiments are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Accordingly, the previously described example embodiments do not define or constrain this disclosure. Other changes, substitutions, and alterations are also possible without departing from the spirit and scope of this disclosure.

What is claimed is:

1. A method of synthesizing an alkyl-caprolactone, the method comprising:
   hydrogenating an alkyl-phenol in a trickle bed catalytic reactor to yield a first stream comprising an alkyl-cyclohexanone and an alkyl-cyclohexanol;
   providing the first stream to a first distillation column to yield a second stream comprising the alkyl-cyclohexanone;
   providing the second stream to a second distillation column to yield a third stream comprising purified alkyl-cyclohexanone;
   oxidizing the purified alkyl-cyclohexanone in a liquid phase fixed bed oxidation reactor to yield a fourth stream comprising an alkyl-caprolactone, the alkyl-cyclohexanone, and the alkyl-cyclohexanol;
   providing the fourth stream to a third distillation column to yield a fifth stream comprising the alkyl-caprolactone and a sixth stream comprising the alkyl-cyclohexanone, the alkyl-cyclohexanol, and water;
   removing some of the water from the sixth stream to yield a seventh stream;
   providing the seventh stream to a fourth distillation column to yield an eighth stream comprising the alkyl-cyclohexanone and the alkyl-cyclohexanol; and
   providing the eighth stream to the second distillation column.

2. The method of claim 1, wherein hydrogenating the alkyl-phenol occurs in the absence of a solvent.

3. The method of claim 1, wherein hydrogenating the alkyl-phenol occurs in the presence of a solvent.

4. The method of claim 3, wherein the solvent is selected from the group consisting of undecane, dodecane, and tridecane.

5. The method of claim 3, wherein the solvent comprises dodecane.

6. The method of claim 3, further comprising removing the solvent from the first distillation column.

7. The method of claim 6, further comprising providing the solvent from the first distillation column to the first reactor.

8. The method of claim 1, wherein the second stream further comprises an alkyl-cyclohexanol.

9. The method of claim 1, further comprising removing unreacted alkyl-phenol from the first distillation column.

10. The method of claim 9, further comprising providing the unreacted alkyl-phenol to the first reactor.

11. The method of claim 1, wherein the fourth stream further comprises an alkyl-hydroxyhexanoic acid, an alkyl-adipic acid, or both.

12. The method of claim 1, further comprising removing hydrogen from the first stream before providing the first stream to the first distillation column.

13. The method of claim 12, wherein removing the hydrogen from the first stream comprises providing the first stream to a flash tank.

14. The method of claim 1, wherein at least 80 wt % of the alkyl-phenol in the first reactor is converted to the alkyl-cyclohexanone.

15. The method of claim 1, wherein less than 30 wt % of the purified alkyl-cyclohexanone is oxidized in the second reactor.

16. The method of claim 1, wherein oxidizing the purified alkyl-cyclohexanone in the second reactor comprises providing an oxidizing agent to the second reactor.

17. The method of claim 16, further comprising reacting substantially all of the oxidizing agent in the second reactor.

18. The method of claim 16, wherein the oxidizing agent comprises hydrogen peroxide.

19. The method of claim 18, wherein the oxidizing agent is provided as an aqueous solution comprising at least 40 wt % hydrogen peroxide.

20. The method of claim 1, wherein the third distillation column is operated under sub-atmospheric pressure.

21. The method of claim 1, further comprising providing the fifth stream to a fifth distillation column.

22. The method of claim 21, wherein the fifth stream further comprises an alkyl-hydroxyhexanoic acid, an alkyl-adipic acid, or both.

23. The method of claim 21, wherein the fifth distillation column is operated under sub-atmospheric pressure.

24. The method of claim 21, wherein the fifth distillation column is operated below 5 atm.

25. The method of claim 1, wherein the sixth stream undergoes heteroazeotropic distillation.

26. The method of claim 1, wherein at least one of the second stream, the fourth stream, the sixth stream, and the eight stream comprises an alkyl-cyclohexanol.

27. The method of claim 1, wherein the alkyl-phenol comprises one or more of:

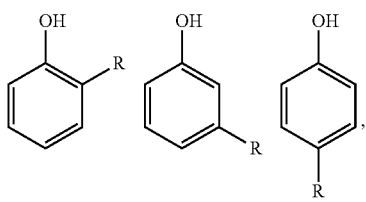

wherein the alkyl (R) is selected from the group consisting of methyl, ethyl, propyl, and iso-propyl.

28. The method of claim 1, wherein the alkyl-phenol comprises p-cresol.

29. The method of claim 1, wherein the alkyl-phenol comprises a compound derived from lignin.

30. A method of synthesizing an alkyl-caprolactone, the method comprising:
   (i) hydrogenating an alkyl-phenol in a trickle bed catalytic reactor to yield a first mixture comprising an alkyl-cyclohexanone and an alkyl-cyclohexanol;
   (ii) separating the alkyl-cyclohexanone from the first mixture to yield a first portion of a purified alkyl-cyclohexanone;
   (iii) oxidizing the first portion of the purified alkyl-cyclohexanone in a liquid phase fixed bed oxidation reactor to yield a second mixture comprising an alkyl-caprolactone, the alkyl-cyclohexanone, and the alkyl-cyclohexanol;
   (iv) separating the alkyl-caprolactone from the second mixture to yield a third mixture comprising the alkyl-cyclohexanone and the alkyl-cyclohexanol;
   (v) combining the third mixture and the first mixture in (i) to yield a fourth mixture;
   (vi) separating the alkyl-cyclohexanone from the fourth mixture to yield a second portion of the purified alkyl-cyclohexanone;
   (vii) oxidizing the second portion of the purified alkyl-cyclohexanone in a liquid phase fixed bed oxidation reactor to yield a fifth mixture comprising the alkyl-caprolactone, the alkyl-cyclohexanone, and the alkyl-cyclohexanol;
   (viii) separating the alkyl-caprolactone from the fifth mixture; and
   (ix) combining the alkyl-caprolactone from the fifth mixture with the alkyl-caprolactone from the second mixture.

* * * * *